US006991464B2

(12) United States Patent
Liebert

(10) Patent No.: US 6,991,464 B2
(45) Date of Patent: Jan. 31, 2006

(54) WEB-BASED MEDICAL DIAGNOSTIC AND TRAINING SYSTEM

(75) Inventor: John A. Liebert, Sedona, AZ (US)

(73) Assignee: Expert Clinical Systems, Inc., Phoenix, AZ (US)

( * ) Notice: Subject to any disclaimer, the term of this patent is extended or adjusted under 35 U.S.C. 154(b) by 329 days.

(21) Appl. No.: 10/319,451

(22) Filed: Dec. 13, 2002

(65) Prior Publication Data

US 2003/0158467 A1    Aug. 21, 2003

Related U.S. Application Data

(60) Provisional application No. 60/344,078, filed on Dec. 28, 2001.

(51) Int. Cl.
G09B 19/00        (2006.01)
(52) U.S. Cl. ............... 434/236; 434/323; 434/362; 600/300; 705/3; 704/270
(58) Field of Classification Search ............... 434/118, 434/236–238, 262, 307 R, 322, 323, 350, 434/362, 365; 600/300, 301; 705/3, 2; 706/15, 706/45, 46; 703/11; 704/270; 702/1
See application file for complete search history.

(56) References Cited

U.S. PATENT DOCUMENTS

| | | | |
|---|---|---|---|
| 4,170,832 A | 10/1979 | Zimmerman | |
| 4,360,345 A | 11/1982 | Hon | |
| 4,895,518 A | 1/1990 | Arnold et al. | |
| 5,385,474 A | 1/1995 | Brindle | |
| 5,454,722 A | 10/1995 | Holland et al. | |
| 5,509,810 A | 4/1996 | Schertz et al. | |
| 5,572,421 A * | 11/1996 | Altman et al. ................. 705/3 |
| 5,574,828 A * | 11/1996 | Hayward et al. ............. 706/45 |
| 5,609,485 A | 3/1997 | Bergman et al. | |
| 5,791,907 A | 8/1998 | Ramshaw et al. | |
| 5,953,704 A | 9/1999 | McIllroy et al. | |
| 6,139,495 A * | 10/2000 | De La Huerga ............ 600/300 |
| 6,193,519 B1 | 2/2001 | Eggert et al. | |
| 6,234,964 B1 * | 5/2001 | Iliff ............................ 600/300 |
| 6,246,975 B1 * | 6/2001 | Rivonelli et al. ............. 703/11 |
| 6,273,727 B1 | 8/2001 | Ramsay et al. | |
| 6,283,761 B1 * | 9/2001 | Joao ........................... 434/236 |
| 6,425,764 B1 * | 7/2002 | Lamson ...................... 434/236 |

(Continued)

FOREIGN PATENT DOCUMENTS

FR        2592514        7/1987

(Continued)

OTHER PUBLICATIONS

Levitt et al., "Computer simulated patients for enhancing Clinical Experiences", (pp. 42-43, Ed-ucational Technology, vol. XVIII, No. 6, Jun. 1978).

(Continued)

*Primary Examiner*—Joe H. Cheng
(74) *Attorney, Agent, or Firm*—Ryan Kromholz & Manion, S.C.

(57) ABSTRACT

An interactive computer system for use in educating and training medical personnel in point of entry triage utilizing multiple visual and audio displays as well as providing access to various other sources of information. The system includes visual, audio and textual interactive display screens that are responsive to input from the user and guides the user through a scenario based upon different conditions presented by the medical patient. The system may be stored on magnetic media or be web-based.

14 Claims, 17 Drawing Sheets

Triage Algorithm

U.S. PATENT DOCUMENTS

| | | | |
|---|---|---|---|
| 6,468,210 B1 * | 10/2002 | Iliff | 600/300 |
| 6,497,577 B2 * | 12/2002 | Kanter | 434/236 |
| 6,556,977 B1 * | 4/2003 | Lapointe et al. | 706/15 |
| 6,853,920 B2 * | 2/2005 | Hsiung et al. | 702/1 |
| 2001/0039503 A1 * | 11/2001 | Chan | 705/2 |
| 2002/0004729 A1 * | 1/2002 | Zak et al. | 705/3 |
| 2002/0010597 A1 * | 1/2002 | Mayer et al. | 705/2 |
| 2002/0035486 A1 * | 3/2002 | Huyn et al. | 705/3 |
| 2002/0072911 A1 * | 6/2002 | Kilgore et al. | 704/270 |
| 2002/0082863 A1 * | 6/2002 | Kleinke | 705/2 |
| 2002/0107824 A1 * | 8/2002 | Ahmed | 706/46 |
| 2002/0132214 A1 * | 9/2002 | Mattson et al. | 434/323 |
| 2003/0120516 A1 * | 6/2003 | Perednia | 705/3 |
| 2005/0165626 A1 * | 7/2005 | Karpf | 705/3 |

FOREIGN PATENT DOCUMENTS

| | | |
|---|---|---|
| JP | 5-257418 | 10/1993 |

OTHER PUBLICATIONS

John A. Liebert, "Computer-enhanced Diagnostics with Disease Specific Management: Best Practices or Worse?"(pp. 1-22, University of Washington Medical Center, Seattle, WA, USA 1994).

Excerpts from presentations, John A. Liebert M.D., "Computer-assisted Diagnosis: Best Practices or Worse?" And "First Encounter: Clinical Assessment for the New Millennium" (pp. 1-36, 2001).

* cited by examiner

**Eye Injury
CHEMICAL**

Continuous, copious and low pressure irrigation of entire eyeball from medial to lateral portion of Sclera with saline solution or cold tap water via gentle stream from IV administration or Eye-irrigating solution*.

Avoid contaminating other eye!

Explain to patient what you are doing to gain complete cooperation in keeping eyelids open wide as possible.

Flush away any particulate matter from conjunctiva and cornea.

Don't stop until tear film is stable at neutral pH.

Rinse eyelids prn.

Topical Anesthetic prn

Place in Emergency Eyewash Station* or Emergency Shower Station* ASAP for use of isotonic irrigation to reduce damage.

Use Wire Lid Speculum* to retract eyelids prn.

Back ⟵ To Fig. 6

*Fig. 5*

Unresponsive Child

I) Tap infant to elicit response.

II) If infant cannot breathe or is UNRESPONSIVE:

A. DO NOT hyperextend neck!

B. Open airway. 

C. If not breathing, ventilate w/ TWO puffs of air – NOT FULL BREATHS!

D. Reposition head & chin and ventilate again with TWO puffs.

E. If UNSUCCESSFUL – Invert infant on arm by supporting, cupping face in hand. 

F. Perform 5 blows between shoulder blades.

G. If nothing comes out, roll infant supine on arm and perform 5 chest thrusts.

H. Look in mouth and remove object if visible.

I. If nothing visible, ventilate.

J. If UNSUCCESSFUL, repeat back blows, then chest thrusts, and mouth inspection. Ventilate until object removed or breathing begins.

Intubate endotracheally if possible when necessary and connect ALS.

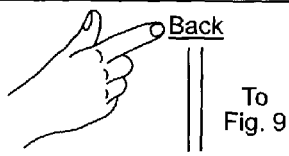

Back To Fig. 9

*Fig. 10*

General Appearance for Intake

Patient is [well-groomed ▼] and [alert ▼] with [normal ▼] consciousness and [free ▼] of cardiovascular-respiratory distress and appears [nourished ▼] and [developed ▼] with [unremarkable odor ▼], [normal ▼] exposed [Caucasian ▼] and [normal ▼] facies. There [is no ▼] evidence of weapons and [no ▼] drug usage, and there is [no need ▼] to protect from imminent situation of violence. Patient [is not ▼] agitated, [is not ▼] combative and [is not ▼] threatening. Patient age? [young ▼] Sex? [male ▼] who [does not ▼] display sociopathy, [can ▼] empathize and communicate, [responds to ▼] limits or direction and [does not ▼] show evidence of fighting wounds. Sensorium and cognition [are normal ▼]. Conative output is [normal ▼]. [There is no ▼] perceptual or aperceptual abnormality. [There is no ▼] thought disorder.

[Reassess]  [Print]

*Fig. 15*

Blue Zone Evaluation

| Question | Answer | | Question | Answer |
|---|---|---|---|---|
| Do you have any medical condition that may take your life right now? | ☐ Y/N | | Marital Status | M ☐ S, D, or M |
| Have you or any one else been concerned that you could physically harm somebody? | ☐ Y/N | | Spouse's Name | Susan |
| Is the patient oriented in all 3 spheres? | ☑ Y/N | | Divorced | ☐ Y/N |
| Date of Birth | 3/11/54 | | Times Divorced? | 4 |
| Address with zip code | 52nd StAnywhere | | Number of Children? | 2 |
| When did you move there? | 5 yrs ago | | Ages of Children? | 11, 14 |
| What type of work do you do? | Financial Analyst | | First name of closest friend or family member? | Larry |
| How long have you been doing this? | 11 yrs | | Does patient feel they need to be there? | ☑ Y/N |
| Highest grade level completed? | 16 yrs | | Chief Complaint? | Pink eye and pain in left eye |
| Year started the last school you attended? | 1982 | | Source | PT-HQ |
| Year completed at last school attended? | 1990 | | Is Anamanesis available? | ☑ Y/N |
| | | | Does patient have any memory loss? | ☐ Y/N |

The last question must be answered to proceed with this Demo.

[Continue]  [Reassess]  [Print]

General Appearance for Intake

Patient is [well-groomed ▼] and [alert ▼] with [normal ▼] consciousness and [free ▼] of cardiovascular-respiratory distress and appears [nourished ▼] and [developed ▼] with [unremarkable odor ▼], [normal ▼] exposed [Caucasian ▼] and [normal ▼] facies.

There [is no ▼] evidence of weapons and [no ▼] drug usage, and there is [no need ▼] to protect from imminent situation of violence. Patient [is not ▼] agitated, [is not ▼] combative and [is not ▼] threatening. Patient age? [young ▼] Sex? [male ▼] who [does not ▼] display sociopathy, [can ▼] empathize and communicate, [responds to ▼] limits or direction and [does not ▼] show evidence of fighting wounds. Sensorium and cognition [normal ▼]. Conative output is [normal ▼]. [There is no ▼] perceptual or aperceptual abnormality. [There is no ▼] thought disorder.

| Reassess | Print |

---

Patient has had increased pain in left eye insidiously progressing. Noticed reddening of eye shortly after pain started two months ago. Denies other significant health history. Appears in mild distress commensurate with pain. Left eye completely injected. Came in today because of heavy travel schedule. Has been using Murine OTC with little relief to date.

Continue 

*Fig. 17*

WEB-BASED MEDICAL DIAGNOSTIC AND TRAINING SYSTEM

RELATED APPLICATION

This application claims the benefit of U.S. provisional application Ser. No. 60/344,078 filed 28 Dec. 2001.

BACKGROUND OF THE INVENTION

The present invention relates to computer assisted medical diagnostic and training systems, particularly web-based (internet) systems.

Medical points of entry, such as emergency rooms, rely on point-of-entry clinicians to triage incoming patients. There is little formal education or continuing education provided to these individuals to enable them to make the daily, specific, time-determined decisions that are necessary at the points of entry. Typically, a clinician makes triage decisions based on individual intuition and knowledge, which varies from one individual to another. Furthermore, as opposed to classical triage in which treatment decisions are made based on real scarcity caused by war or poverty, "triage" in the modern health setting includes artificial scarcity caused by contemporary demand management. This contemporary notion of triage implies an effort to enhance quality while simultaneously reducing the costs of healthcare delivery at points of entry.

The present invention is a web-based expert system for teaching "time-determined" clinical triage decision-making made at medical points of entry. The system models the thought process of clinicians performing best practices. The infrastructure of navigational specifications is based on generally accepted principles of clinical decision making within a time constraint framework. The present invention will be embedded within a known navigational system, which will serve to open and navigate the invention.

Alternatively the present invention is a web-based expert system for assisting triaging at medical points of entry.

SUMMARY OF THE INVENTION

The system of the present invention includes a web-based computer system having a display, wherein the computer system is programmed to provide education and training in point of entry triaging procedures, and to further cooperate and interact with known computerized products, such as the CLINICMASTER™ by Sirius Technologies. This aspect is achieved by configuring the system to display virtual reality simulations or audiovisual segments demonstrating triaging procedures. Means is provided for requesting a user to input information relating to ongoing triaging decisions. Corresponding means are provided for receiving user input, and may be provided in the form of a keyboard, a mouse, a touch-sensitive screen, or any number of other input/output devices used in connection with a typical computer system. Responsive to the information input by the user, additional means are provided for interpreting the information and informing the user as to whether the input is correct.

The system of the present invention preferably includes virtual reality simulations or audiovisual segments to aid in tutorial. A pop-up assistant or help feature prompts a system user as required during the tutorial, based on ongoing user decisions. The user/student navigates through the various screens, and makes time-critical triage decisions based on the facts presented by the program. The student is required to make appropriate fact-based clinical decisions, and additionally is required to make them within a clinically accepted time frame. For example, a display screen may present a fictional patient having certain symptoms that would normally lead to immediate critical treatment, including predetermined diagnostic tests being performed within a very short time frame. The program will respond in the event the user makes improper choices such as delaying performing certain diagnostic tests or routing of the patient to a non-critical zone by prompting the user to consider the choice made. Also if the user delays inputting a response within a predetermined time frame, the program prompts the user to reconsider the choice made.

The invention also includes hyperlinks to available medical information technology, such as virtual reality for replication of diagnostic information such as tactile and olfactory information.

It is an object of the present invention to provide a web-based device for educating and training personnel for triaging medical patients at points of entry.

It is another object of the present invention to provide an improved web-based educational and training device providing an interactive user environment.

Yet another object of the present invention is to provide a web-based triaging tool for point of entry application.

Additional objects, advantages and other novel features of the invention will be set forth in the description that follows and in part will become apparent to those skilled in the art upon examination of the following or will be learned with the practice of the invention.

To achieve the foregoing and other objects, the present invention is generally directed to a web-based interactive triaging training device and point of entry tool.

DESCRIPTION OF THE DRAWINGS

FIG. 5 shows an example of a tutorial display screen built into the system.

FIG. 10 is another example of a tutorial display screen built into the system.

FIG. 15 shows a continuing link for from FIG. 14.

FIG. 16 displays a link for assessing a situation of low medical priority.

FIG. 17 is a continuing link from FIG. 16.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention.

Figure 1:
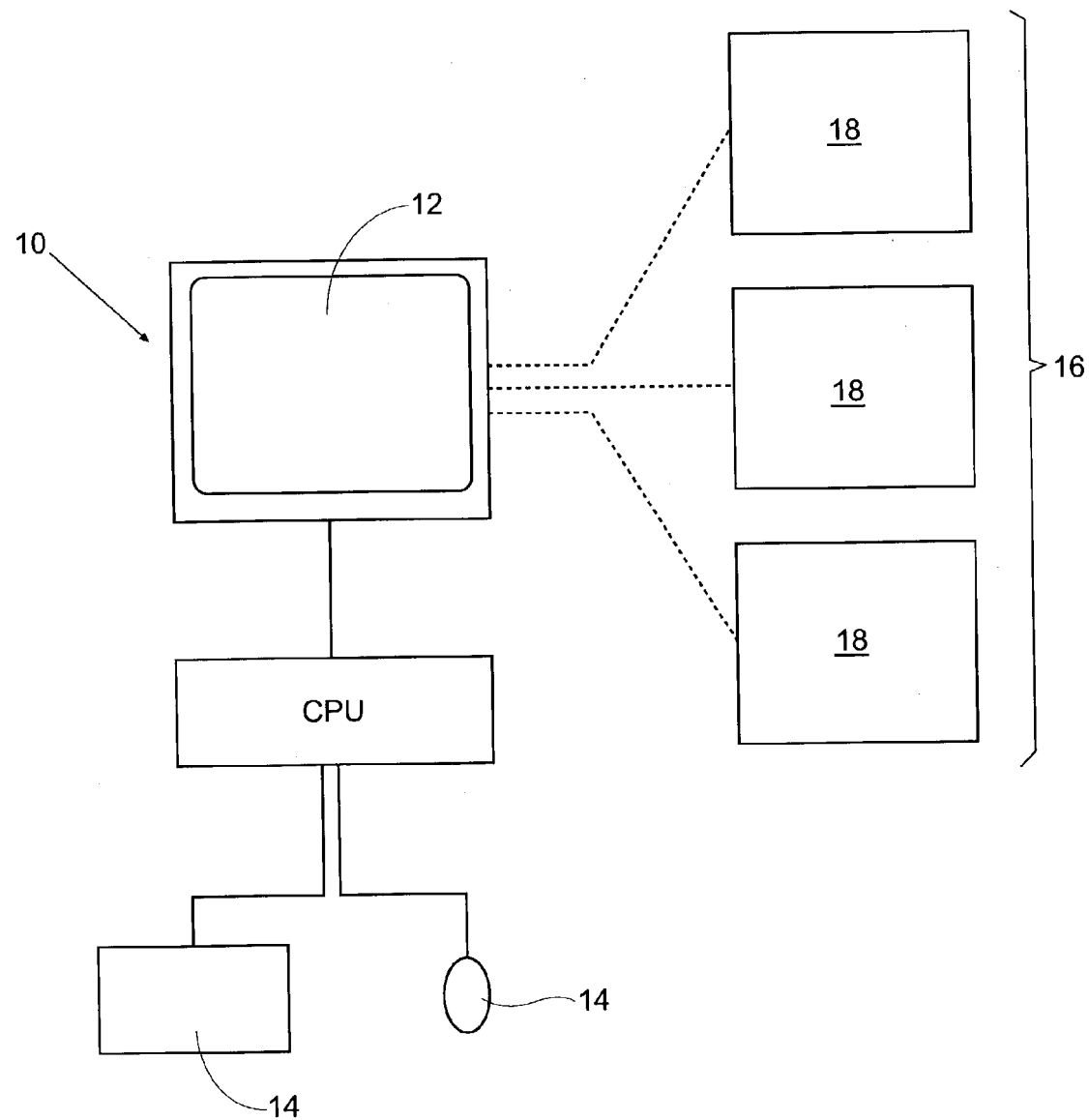
FIG. 1 is a schematic block diagram illustrating a general-purpose computer linked to a website in which the present invention may be practiced.

The system of the present invention is based in an expert system developed and stored on magnetic media, such as CD-ROM and additionally designed for web-based application, for supporting education and best practices in triaging patients at points of entry into the healthcare system. As seen in FIG. 1, the system of the present invention includes a computer system 10 having a video display 12, a user interface device 14, seen as a peripheral mouse or keyboard, a linked website 16 including a plurality of stored textual, audio and/or video display screens 18 relating to decision making steps in medical triage. The computer system 10 is provided with a navigational program to provide education and training. This system is preferably used in a web-based environment and knowledge based system utilizing auto tutor and virtual reality technologies. The system is based substantially on standard emergency medicine navigational specifications and protocols of clinical science. However the system of the present invention includes several unique features.

Figure 2:
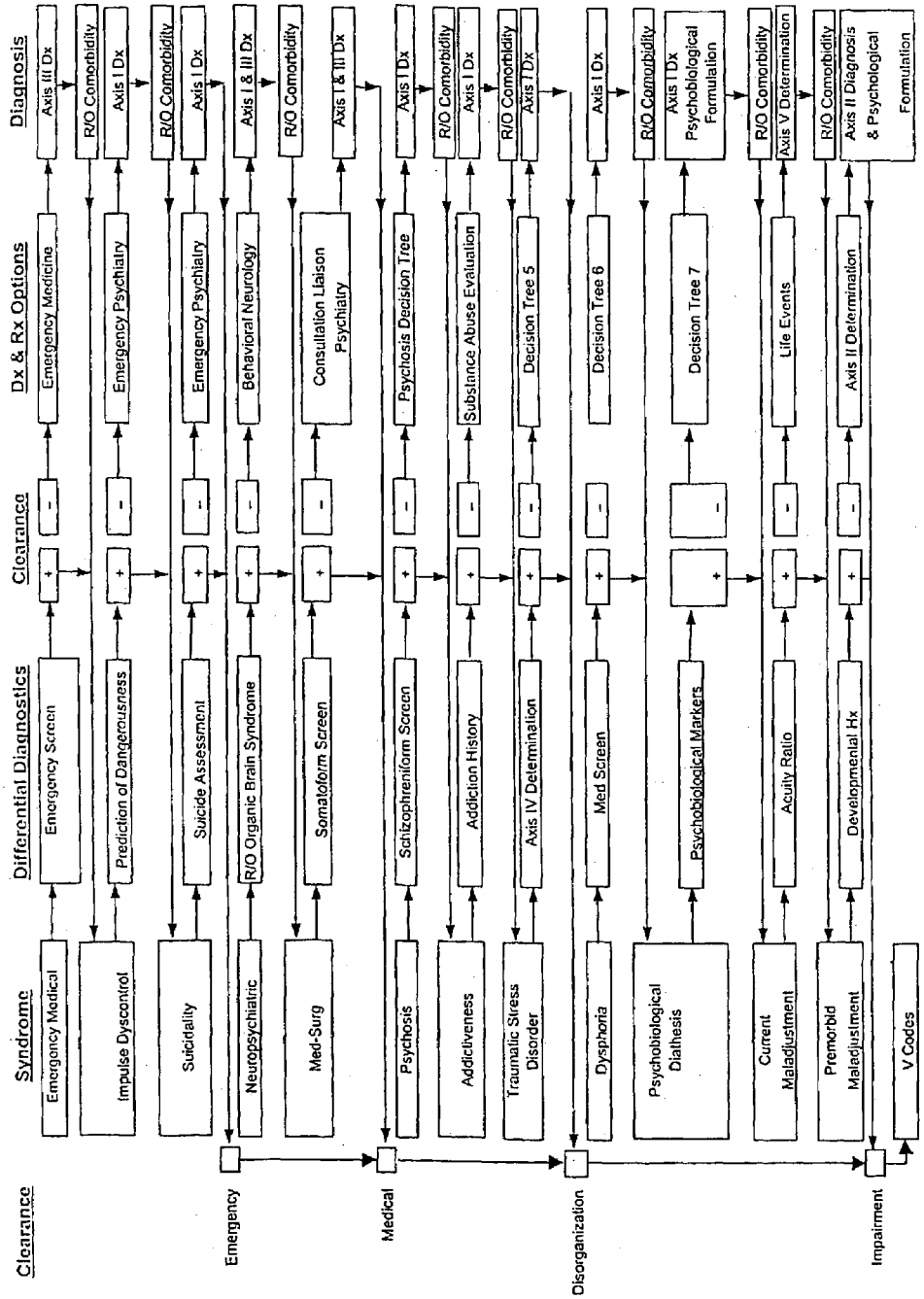
FIG. 2 is a block diagram of a flow chart representing the system of the present invention, seen as the Triage Algorithm.

The system of the present invention provides web-based tutoring for health professionals and students regardless of geographical location, and is especially helpful for distance learning. The basic navigational system used for opening the system and navigating through the screens is preferably the Triage Algorithm, as seen in FIG. 2. The algorithm is preferably embedded in the navigational system and functions similarly to an electronic direction board in a transit station. The basic prioritized sequencing of triage track on the Triage Algorithm includes:

A. Emergency Medicine
B. Dangerousness to Others
C. Suicidality
D. Neuropsychiatry
E. Medical/Surgical
F. Psychosis
G. Addiction
H. Traumatic Stress Disorder
I. Dysphoria
J. Psychobiological Diathesis
K. Current Maladjustment
L. Premorbid Maladjustment Each of the sequenced and prioritized clinical pathways included above in A–L are shown as colored lines or tracks on display screens, similarly to colored transit station routes, as for example in a subway station. The system further displays movement on the tracks by way of railcar or other suitable image, with movement starting and stopping at labeled stations. The stations are preferably labeled according to destination (e.g. "Emergency Room"). The stations are lit and vary in action according to the desired user response. For example, a flashing station may mean stop, while a steady signal may signal pass. Associated syndromes and clinical problems that are to be addressed may be added to the movement by, for example, adding cars to the moving railcar. By way of example, a hypothetical patient presented on the system as diagnosed with anthrax may preferably be depicted on the display screen as carrying a plurality cars, "infectious disease", "bioterrorism", and "posttraumatic stress disorder".

In use as an auto-tutoring device, the present invention may utilize a number of visual tools including virtual reality simulations or video demonstrations of clinical procedures. The auto-tutoring aspect preferably includes a help feature. The help feature may be invoked spontaneously, or as a result of user decisions. Preferably, the help feature displays pre-recorded video segments of a doctor instructing the user or prompting the user as to procedural steps to be followed. Both video and sound may be output to the user.

The "Begin Diagnostics" screen preferably presents a plurality of colored tabular options to the user. The colored tabs are color calibrated to specific time frame choices to be made for the presented clinical scenario. The help feature prompts the user to the function of each colored tab. For example, the student is instructed to select the red tab if the patient may not safely wait for definitive clinical intervention; orange tab if the patient may safely wait briefly without causing death or permanent disability; yellow tab if the patient may safely wait more than fifteen minutes or be worked up within an hour; green tab if the patient may safely wait for an hour or be worked up within two hours; and blue tab if the patient may safely wait for three hours or be worked up within four hours. The user uses an input device to select the appropriate tab. It is to be noted that the tabs may also be voice activated.

Tab activation causes the screen color to change to the selected tab color. Additionally, the selection of tab color adds a separate functionality to require the user to judge safe waiting times for both initial assessment and clinical intervention.

Should the user fail to select the appropriate clinically indicated tab by indicating a less urgent state than is necessary for the exhibited patient symptoms, the screen immediately displays black, and a flashing banner message indicates the clinical feature missed by the user in selecting the inappropriate treatment time frame. The help feature is then preferably displayed and a brief analysis of the missed clinical feature is presented to the user. The help feature may further include screen displays illustrating salient diagnostic clinical features.

Should the user select a more urgent time frame than that indicated by the exhibited patient symptoms, the screen displays red, and the help feature is displayed. The help feature may, for example, provide a brief lecture regarding the features of the missed diagnosis. Should the user select the correct time frame for the clinical features present in the hypothetical patient, an orange screen is displayed showing complete lighted clinical tracks and several additional features. Additional features displayed on the orange screen may include a clock timing insert showing timing of the decision-making process, or a tabulator insert indicating approximate cost at patient time of entry and during clinical decisions making, including for example, diagnostic tests made after patient entry health care location. The help feature may be further displayed to prompt the user to select clinical pathways from the displayed orange screen. This screen prompt is also preferably displayed after incorrect answers, and after the user has viewed the red or black screens following an incorrect time analysis.

From the orange screen the user preferably selects a "line" using user input means. The selected line lights up indicating its selection and a train car is activated to move toward a triage station. As the car arrives at the station, the help feature is activated and the user is prompted to select patient presentation options as shown. Some examples of selections available include "sick adult" and "shortness of breath". The user selection causes the triage station display to enlarge into protocols for the combination of time frame selected and presentation options selected. As long as the user correctly works up the hypothetical patient, the help feature prompts the user from decision to decision. During correct patient work up, time is preferably clocked from point of patient entry, and cost is tracked for both time and interventions selected. If the user makes an incorrect decision that jeopardizes the patient, the flashing red screen appears with a running banner describing the error.

If the user performs the simulated workup correctly and within a safe period of time, the help feature preferably appears as a medical expert in the field presented by the symptoms of the hypothetical patient. The expert help feature then preferably delivers a lecture on differential diagnosis. Included in this lecture may be, for example, bioterrorist infections.

The orange page of the system is preferably provided with a plurality of hyperlinks. Hyperlinks provided may include navigation to web-based systems such as, but not limited to:
1. The dictionary of the Digital Clinician 2, or a suitable similar reference.
2. Computer Diagnostic Support Systems, such as Scientific America, by way of example.
3. Virtual reality simulations of surgical procedures, palpation and abnormal body odors.
4. Videotapes
5. Clinical images and sounds.

By way of illustration, if the user has accessed the expert help feature of an infectious disease expert, the user may selectively hyperlink to
1. Computer Diagnostic support system links with infectious disease and bioterrorism tables of content.
2. Sounds and images of all dermatology lesions, in the format of prepared slides, which the user may enlarge through selection. All differential diagnostics for the presented symptoms are accessible by the user. Additionally, the user may access simulated sounds of, for example, heart and respiratory systems of patients having similar hypothetical symptoms.
3. Virtual reality links that allow the user to "perform" procedures on hypothetical patient in an ICU setting, including but not limited to experiencing jugular venous pressure and symptomatic odors.
4. Search dictionaries having definitions of words used in protocol text or in auto tutorial lectures provided by the help feature.

The user is given a predetermined amount of time to select a hyperlink after the expert help lecture, after which the help feature preferably prompts the user to select further relevant clinical pathways that must be ruled out to prevent comorbid exacerbation of the patient. The user is given a predetermined length of time to respond by choosing to remain in the ICU virtual reality setting, terminate triage, or select additional "tracks". Should the user elect to remain in the ICU setting, an interactive workup of the hypothetical patient is presented. To begin the workup, the user must select the patient's clinical state of awareness. During this selection, the user should not select the green or blue zones, since this indicates that the user judges the patient to be chronically ill and able to wait two or more hours for clinical intervention. As the user moves back and forth among red, orange and yellow zones, treatment protocols or interactive questions and answers are provided. If for example, the user views "eye problems" in the yellow zone, along with all protocols, the user will also view bundled necessary information regarding ophthalmology for a one hour encounter with an unknown patient having an eye problem. The user may select from among many time-determined bundles of information. The bundles may be selected from a predetermined medical specialty, physiological system, or disease.

Alternatively, if the user chooses to close triage for the hypothetical case, the screen will flash red and a banner scrolls across the screen advising the user to select another "line", such as the aqua line, leading to another station. The user inputs a choice, such as "traumatic stress" and the train car moves on aqua line to the station labeled "Critical Incident Stress Debriefing". The car may be coupled with additional cars, such as, for example, "Post/Traumatic Syndrome". The screen may display an interview session illustrating an interviewer in an interview situation. The interviewer prompts the user to select from a menu of interactive choices such as:
1. Dictionary defining the syndrome at issue, for example, post traumatic stress syndrome.
2. Computer diagnostic support links including text and/or didactic learning materials on the syndrome at issue.
3. Virtual reality options including an actual counseling session.
4. Images and sounds including real-time dissociative experiences in which the user may select the experience most suggestive of the syndrome at issue. Cost of the test is also registered along with measurement of workup time.
5. Question and answer in which the help feature presents questions to the user regarding patient management, for example, family, authorities, administration and media.

After exit of the counseling room, the station is displayed on the screen. The train displayed may include a plurality of cars bearing associated syndromes, or comorbidity. The user is given a predetermined amount of time to select an option. Unless the user selects to proceed with diagnosis and treatment, the screen goes red. The student is given visual and verbal feedback as to the appropriateness of selections made. For example, in some circumstances, selecting green or blue tabs will invoke a fading red screen having a text banner message indicating that medical surgical care has been dangerously neglected.

If the user selects the blue or green tab while in the station labeled "Critical Incident Stress Debriefing", the help feature is invoked. The help feature preferably instructs the user on how to handle the presented clinical situation, such as instruction to reduce psychiatric complication for patient family and relevant others. Should the user select any other colored lines, the lines go dark. The user may choose to terminate triage after the Critical Incident Stress Debriefing lecture. If triage is terminated, the user is prompted by the system to either select to triage another case or take a final examination as administered by an expert on the case. If the user selects another case, the screen will display the lighted clinical track map, with timer and cost tabulator displayed, followed by a hypothetical clinical presentation.

The present device is open ended, allowing for use in conjunction with other navigational systems and emerging clinical advances. Additional tabular displays may be conceivable and those presently used by be modified and not depart from the spirit and scope of the invention. Further, the diagnostic and clinical management information included in the present invention is preferably bundled into time-determined bundles or packets, as seen in The Digital Clinician 2, for example. The comprehensive clinical tracking system for The Triage Algorithm is preferably embedded into The Digital Clinician 2. The help, or auto-tutoring feature may include "talking heads" delivering salient lectured material, videotaped presentations, or virtual reality interactive sessions, by way of example. Other useful help features may also be envisioned.

The Triage Algorithm seen in FIG. 2 is a visual representation of the clinical pathways and stations or nodes located along them. Each "station" opens to a realistic clinical setting and couples comorbidity "cars" to the navigating train. The system of the present invention is preferably linked to hyperlinks available in relevant medical informatics technology. This feature is a novel innovation for distant education in clinical decision-making for health professionals. The following examples will further exemplify the current invention.

EXAMPLE 1

Emergency

Emergency conditions are preferably represented by a red line and red screen. The system is designed to ensure that by grouping specific related symptoms at different intervals, the most life threatening injuries and conditions are treated first. As may be seen, the system uses mnemonics to assist user recall under the real life pressured circumstances of emergency presentations.

Figure 3:
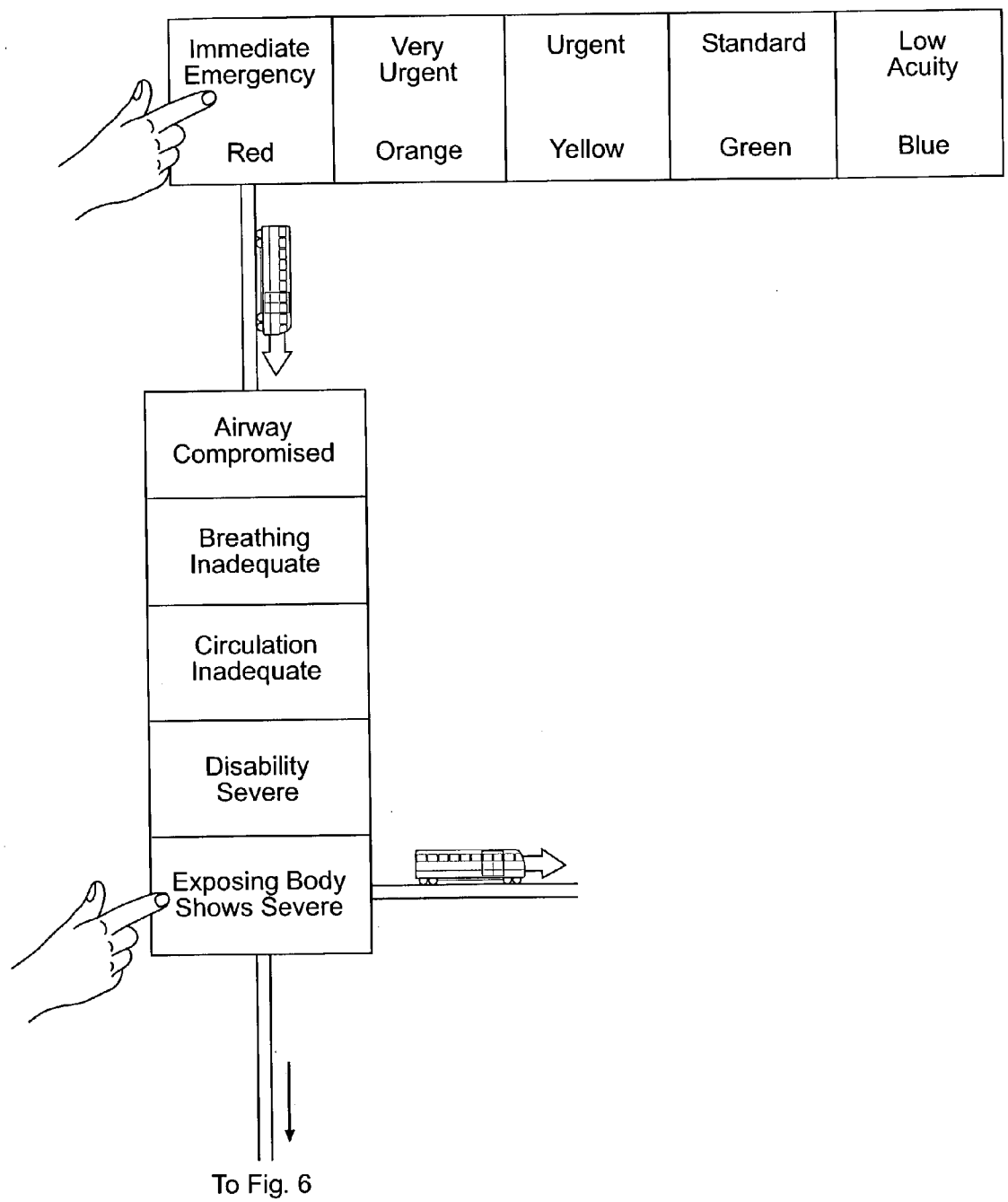
FIG. 3 is a flow chart illustrating an initial emergency assessment screen of the present invention including selection of the red Immediate Emergency line.

For instance, an example patient to be treated may be a young child covering her eye. The user determines that the child is in severe pain and selects, as shown in FIG. 3, the Immediate Emergency tab for diagnosis, which is represented by a red screen and red line.

Figure 4:
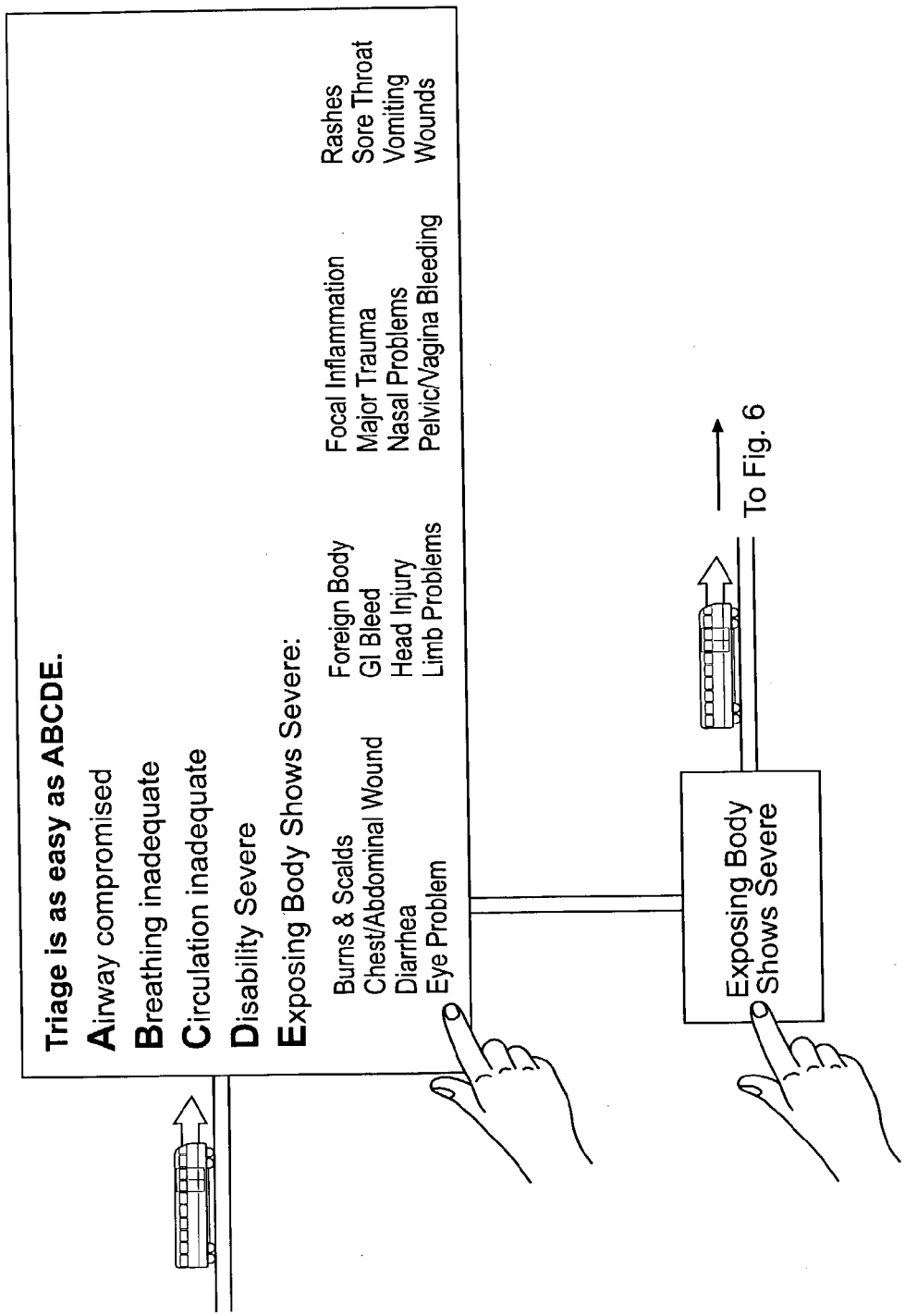
FIG. 4 illustrates a display screen with a flow chart showing the selection of an eye injury.

Once selected, the simulated subway car proceeds to the next station where a user is presented with what is considered the five most critical "ABCs" of triage. The five categories presented as the "ABCs" are:

Airway Compromised
Breathing Inadequate
Circulation Inadequate
Disability Severe
Exposing Body Shows Severe:

When the system is used for training purposes, the user must contemplate all of the five categories before the user is allowed to proceed to the next station. In the present example, the user should choose "Exposing Body Shows Severe:", which allows the subway car to proceed to another station that lists specific body injuries, which can be seen in FIG. 4. At this station the user selects "Eye Problem". This choice prompts the car to move to another station showing possible acute eye problems. By selecting one of the presented eye problems, the user prompts the screen to present the differential diagnosis of acute eye problems requiring immediate treatment intervention.

Of all the possible eye injuries, only chemical injury, the user will see, requires as immediate a treatment as the other "ABCs" of the first station to thereby prevent the permanent morbidity of blindness. If a chemical injury is deemed to be the correct diagnosis, the screen will give instructions for immediate care, as shown in FIG. 5. For educational purposes, optional links lead to useful websites, such as The Dictionary of The Digital Clinician, ophthalmological virtual reality sites elsewhere which provide the user with the actual experience of, for example, using eye wash equipment on a virtual patient, or still and moving images of instruments and technique, accompanied by autotutorial lectures on diagnosis and treatment of chemical eye injuries.

Also, an optional chat room allows users to communicate with one another about the management of a particular injury, and e-mail functions allow users to communicate with the ophthalmological authority represented by the autotutor talking head. As for all diagnoses, any one or all of these features may be available, but the system is designed as an open platform to access all other platforms rapidly becoming available, thus compelling the web master to maintain timeliness for currently authoritative information. Optionally, banners on the chat room site may allow medical instrument vendors and pharmaceutical companies to present testimonials, perhaps in response to autotutorial authority or emails from users. This feature is the equivalent of a real-time medical letter containing input from pharmaceutical companies, for example to support or refute statements from an "objective source".

Figure 6:
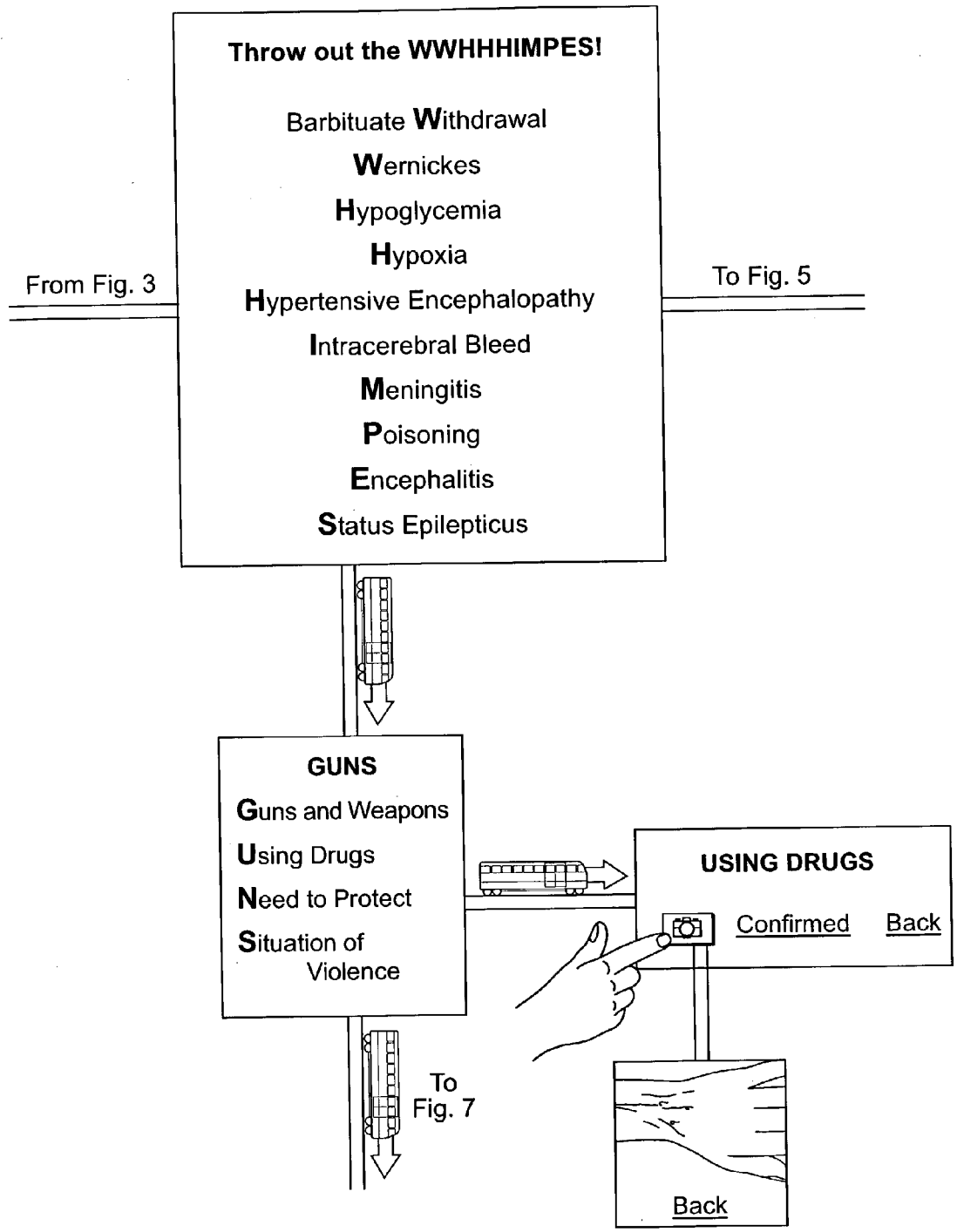
FIG. 6 is a continuing flow chart of an emergency assessment.

In the example, if the presented injury is not a chemical injury, but another eye injury that is not life threatening or an imminent loss of sight, the system directs the user back to the main red line, and allows the user to proceed to the next station. The next station, and as seen in FIG. 6, uses another mnemonic, WHHHIMPES, to determine eight emergency situations regarding altered states: Withdrawal, Wenrickes, Hypoglycemia, Hypoxia, Hypertensive Encephalopathy, Intra Cerebral Bleed, Meningitis, Poisoning, Encephalitis, and Status Epilepticus. It should be noted that the WHHHIMPES station is an example of organizing differential diagnosis into time-determined bundles of information. The present system includes hundreds of causes for altered states of consciousness, but only knowledge of the eight represented in the mnemonic is needed to prevent death or morbidity from failure to intervene immediately upon presentation. Other causes that may be equally dramatic in presentation, therefore, can safely wait until after higher priority presentations are attended to.

After the WHHHIMPES station is properly exited, the subway line is directed to a station that deals with assessing a dangerous situation. The "GUNS" station assists the user in an interactive learning situation. The user is dramatically informed of skipping these steps by a visual aid, such as the screen flashing similar to an emergency vehicle light bar, thereby dramatizing that violence has occurred at point of entry due to failure to observe for evidence of weapons (G) and proper disarming of patient; drug Usage (U) i.e. needle marks on forearms, Need to protect (N), as evidenced by fear patient has for immediate safety from a real threat to his or her life and (S) Situation of violence, as evidenced by a sullen, or even an arrogant, attitude. This requires checking the facility grounds for other persons potentially threatening to patient or site itself—i.e. terrorists or gangs.

Selecting any of the four letters of the GUNS station directs the user to a related link, which displays useful information for the specific situation. For instance, if the user is not sure whether the presented patient uses drugs, selecting the "U" link, provides access to images of skin lesions caused by IV drug usage. This added information allows the user to either confirm or rule out drug use in the presented patient.

Figure 7:
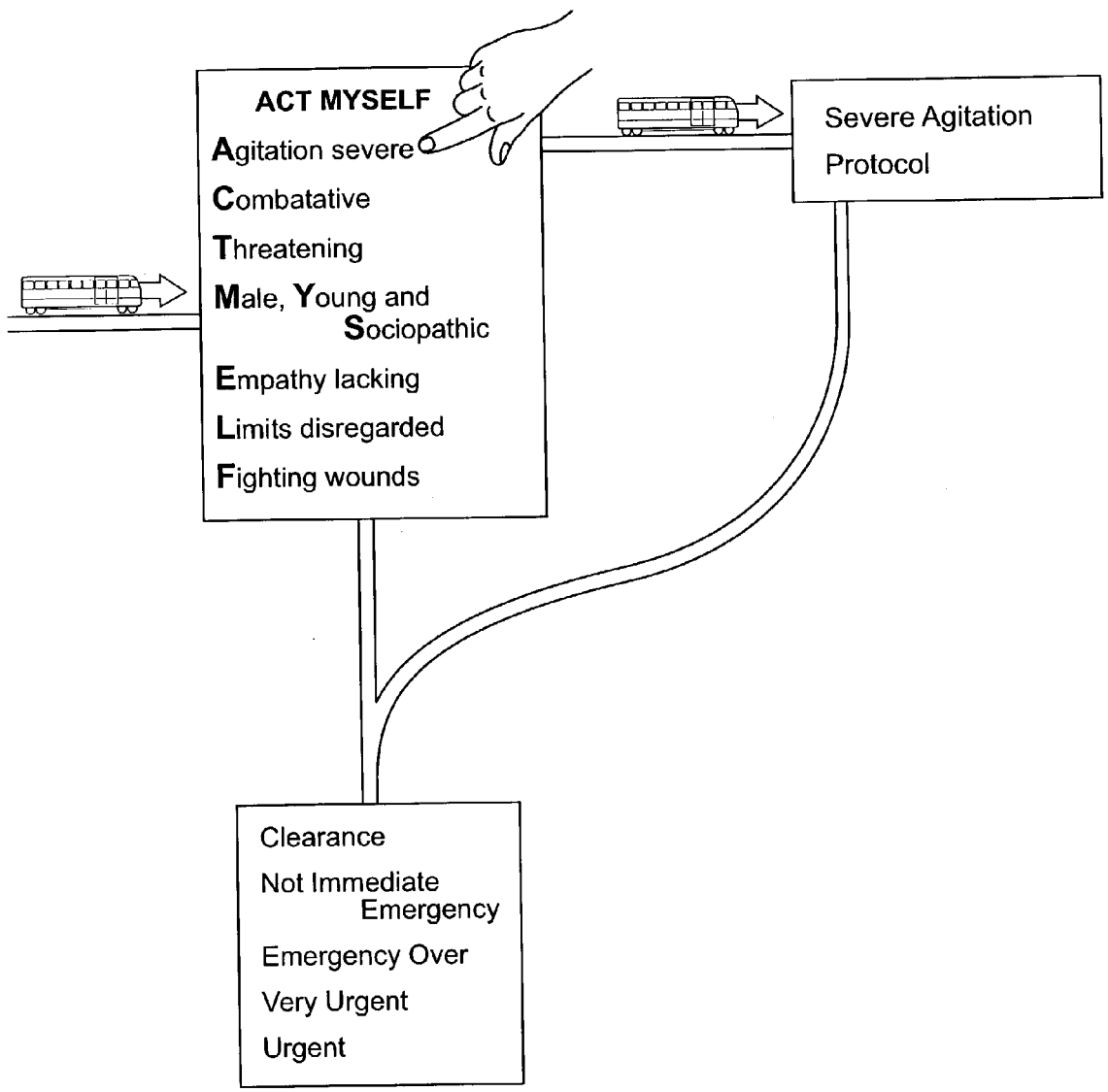
FIG. 7 further continues the emergency assessment flow chart.

After the "GUNS" station has been successfully passed, the subway line passes to another station, the "ACT MYSELF" station, as shown in FIG. 7. This station further assesses the presented patient's state of mind. As may be seen in FIG. 7, the assessment may be analyzed as follows:

Agitation severe
Combativeness
Threatening
Male, Young, and Sociopathic
Empathy Lacking
Lacks Disregard
Fighting Wounds.

As with the other stations, each letter links to another page that lists rules and instructions for how to deal with the indicated element. For instance selecting "agitation, severe" provides the user with possible medical restraint protocol, including possible drugs for soothing the situation. As mentioned previously, the system may further provide links to various updates, including for this example, currently prescribed drugs. As known in the art, the currently used drug for combating such a situation, IM Haldol, may be replaced soon with a safer compound, Geodon; the system can be linked to update such information.

At any of these stations, if an emergency is detected proper actions may be input. However, if all of the preceding stations are passed with negative results (no problems encountered), the system directs the user to another station, which allows the user to enter what is coded as the orange line. The orange line directs the user in situations considered very urgent but not as urgent as those encountered in the red line. For instance, if the child with the injured eye presented in the red line did not have any other problems, and the eye injury was not chemically induced, the diagnosis would lead the subway car to the end of the line, which would give assessment criteria for the very urgent, or orange line. As a training tool, the system allows the user to progressively navigate the screens from highest to lowest levels of lethality or danger.

EXAMPLE 2

Figure 8:
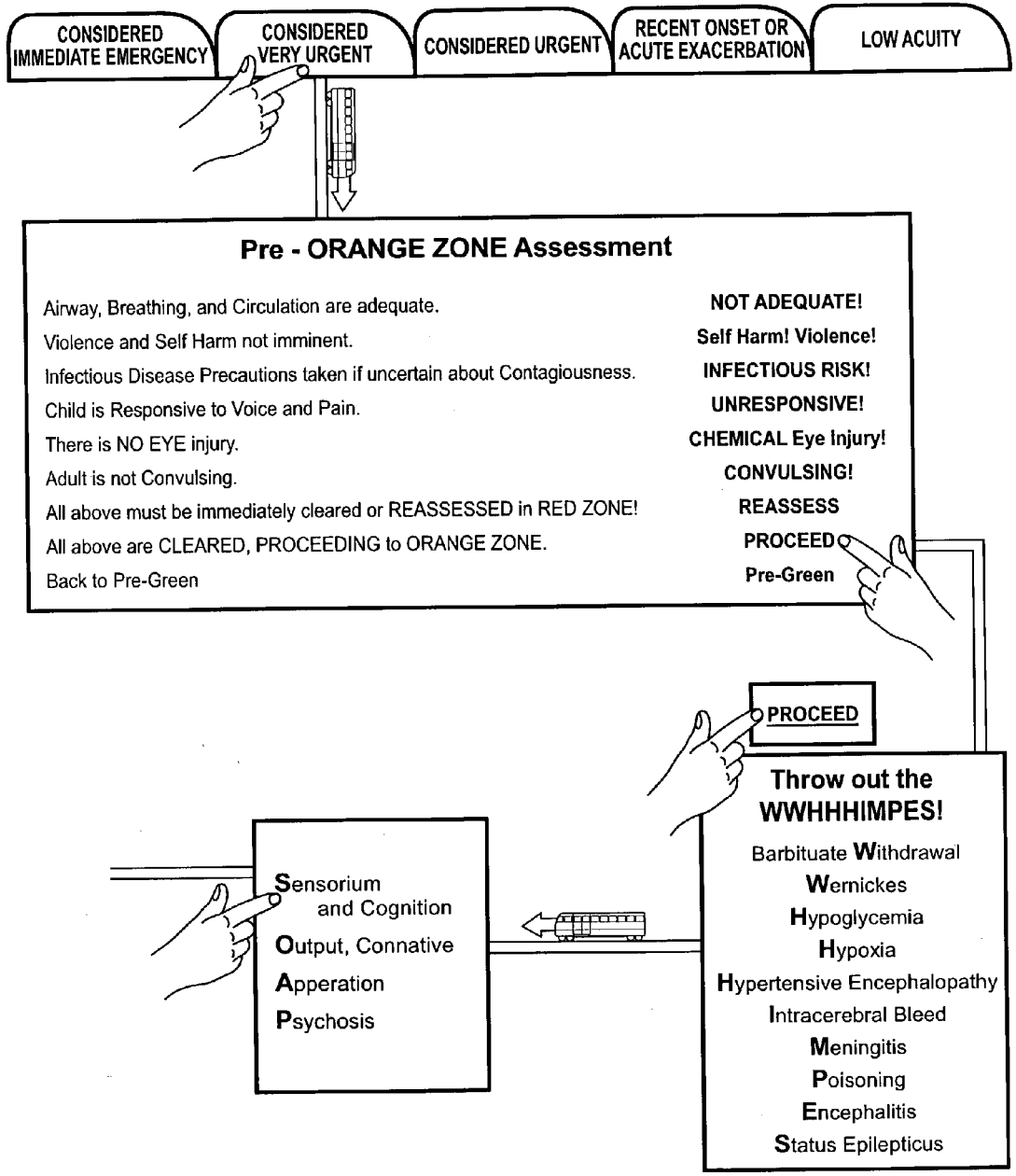
FIG. 8 illustrates a display screen showing a flow chart for assessment of a very urgent medical condition.

Conditions that are considered very urgent but not life threatening are shown as an orange subway line. For example, the child from example 1 enters with an eye injury. The injury looks severe, but is not determined to be cause by a chemical burn. As seen in FIG. 8, the user selects the very urgent, or orange line to proceed with a diagnosis.

As seen in FIG. 8, the first station on the orange line preferably includes prompts to aid the user in verification that the user has cleared all emergency situations, such as that airway, breathing, and circulation is adequate, the patient is not violent, the patient is responsive and not convulsing, and the patient has not suffered a chemical eye injury. If any of the above criteria are not met, the system will redirect the user to the emergency red line of the system. If the above criteria are met, the system allows the user to proceed along the orange line.

The next station on the orange Very Urgent line is the same WHHHIMPES station seen previously in FIG. 6 with reference to the red Emergency line. This station prompts the user to determine eight emergency situations regarding altered states: Withdrawal, Wenrickes, Hypoglycemia, Hypoxia, Hypertensive Encephalopathy, Intra Cerebral Bleed, Meningitis, Poisoning, Encephalitis, and Status Epilepticus. The WHHHIMPES station, it should be noted, is an example of organizing differential diagnosis into time-determined bundles of information. This station is preferably built into both the red Emergency and orange Very Urgent lines to ensure that the user does not overlook potentially life-threatening situations. Once the station is passed, the user may proceed to the next station along the line.

Figure 9:
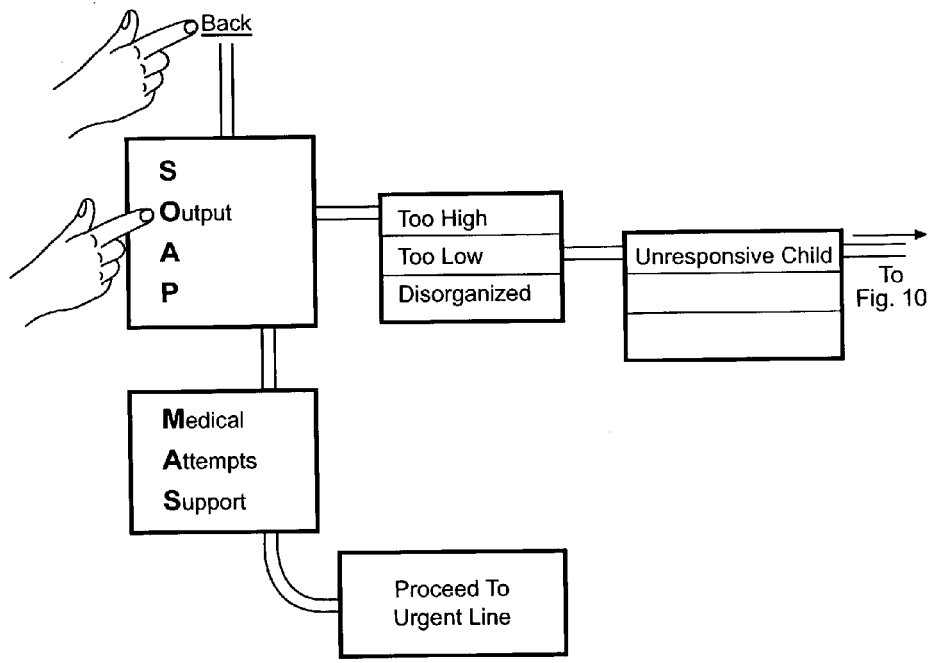
FIG. 9 is a continuation of the flow chart in FIG. 8.

The next station prompts the user to analyze the vital signs of the presented patient. As shown in FIG. 9, the user is presented with an acronym, SOAP, to facilitate the user's ability to properly diagnose the presented patient's symptoms. If for example, the user selects S, for Sensorium and Cognition, the system links the user to another station in which the user is prompted to query the patient with general information seeking questions, such as name and date. If the patient has difficulty answering any of these questions, or appears disoriented, the user is rerouted to the red emergency line for reevaluation. If the patient appears lucid, the user will be directed back to the SOAP station.

As seen in FIG. 9, if the user selects O, for Output, the system links the user to aids in assessing the presented patient's exhibited characteristics. For instance, if the child presented in the example is unresponsive and that characteristic is entered in the system, the user is linked to a tutorial, seen in FIG. 10, showing steps in restoration of breathing. The tutorial gives directions how to revive the child, including links to photographs of relevant situations. If the patient's output appears normal, the patient can continue at the SOAP station.

If the user selects A, for apperception, the system links to aids to help the user determine whether the presented patient may be overtly paranoid or hallucinating. If either of these situations is present, the user follows the A link further to determine whether the patient is a high risk to herself or others. In this instance, the user would once again be rerouted to the emergency line. If not, the user may proceed further at the SOAP station.

The final link at the SOAP station, P, allows the user to determine whether the patient exhibits any psychotic symptoms. If the presented patient exhibits psychosis and potential harm to others, and this information is input into the system, the system directs the user to the red Emergency line. If no such information is entered, the user is directed to proceed to the next station on the line.

The next station presents bundled information to assist the user in further determining the extent of the presented patient's injury. In the present example, the user can select eye injury from the Medical link, causing the system to link to possible eye injuries. Once linked to possible eye injuries, the user is presented with choices to link to specific problems, such as globe rupture or recent loss of vision. Once the user selects a specific problem, the system presents a tutorial showing proper treatment for the selected injury. After assessing the injury, this system further prompts the user to determine whether the patient is a threat to other patients or is, a possible suicide risk. If either of these options is selected and input into the system, the system redirects the user to the red emergency line. Alternatively, if the user passes through this station without prescribing any treatment for the patient, the system presents a next station, linking to the yellow Urgent line.

EXAMPLE 3

A user selects the yellow Urgent line in situations in which the presented patient shows symptoms not overly severe. For example, the hypothetical child may be presented with a hand over one eye, appearing lucid and relatively calm, in pain, but appearing to handle the pain. In this instance the user selects the yellow Urgent line.

Figure 11:
FIG. 11 illustrates a display screen showing a flow chart for assessing an urgent medical problem.

The first station of the yellow Urgent line is shown in FIG. 11. As seen, selections regarding the how and why of patient arrival are also presented, in addition to assessment options. The first station on the yellow line prompts the user to analyze the patient for any contagious diseases, such as herpes, chicken pox or the mumps. The station supplies links to each of the diseases. The links contain information about each disease, including for example, pictures, disease transmittal, and precautions. If a disease is selected, the user will be directed to reassess the situation. If not, the user is prompted to proceed to the next station.

Figure 12:
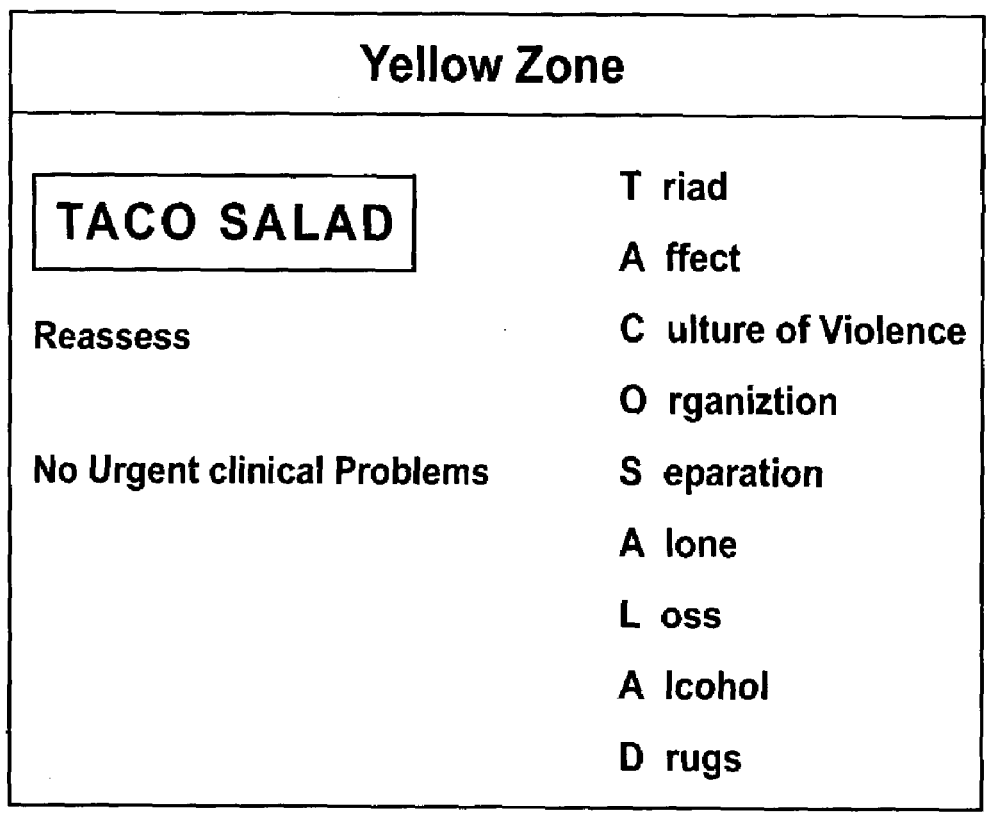
FIG. 12 is a continuation of the flow chart in FIG. 11.

As shown in FIG. 12, the next station, coined TACO SALAD, assists the user in determining more extensively the nature of the presented patient's symptoms. The TACO SALAD mnemonic stands for:

Triad
Affect
Culture of Violence
Organization
Separation
Alone
Loss
Alcohol
Drugs.

The TACO SALAD station functions as a gateway station for further diagnosis on the yellow Urgent line.

If the user selects Triad, the system links to a station that prompts the user in determining the impulse control of the patient. If the patient has difficulty with impulse control or has a history of violence, for example, the user is prompted to reassess the situation. If none of the questions asked prompts a positive (yes) response by the user, the user is prompted to return to and continue at the TACO SALAD station.

The next two links at the TACO SALAD station, Affect and Culture of Violence, also direct the user through a battery of questions to assist the user in determining whether the presented patient is considered harmful or dangerous. As with the Triad link, negative responses prompt the user to continue at the TACO SALAD station.

At the Organization link, the user is prompted to determine the extent of the patient's mental organization. The Organization link also prompts the user to assess whether the patient has more severe problems, such as liver failure, which require urgent attention. If such a symptom is entered, the system directs the user to a relevant tutorial. If no such problems are entered, the user is prompted to determine whether the presented patient is disorganized, such as if the patient appeared drunk. If the patient's disposition is entered as normal, the system prompts the user continue the assessment.

The next three links at the TACO SALAD station, Separation, Alone, and Loss, assist the user when the presented patient displays serious psychological problems. The user works through the three links as the system prompts the-user to answer questions to indicate whether the patient has more serious problems that may not be visible. The questions present to the user reinforce the concept that potentially harmful situations should not be overlooked in any stage of patient evaluation. In the present example, for instance, if it is determined that the child does not have a chemical injury to the eye and appears to a have non-serious eye injury, but the child isolates herself and is in an agitated state, the system assists the user in determining whether there is more serious problem needing immediate attention. In this way the system assists the user in performing a thorough patient analysis.

The final two links at the TACO SALAD station, Alcohol and Drugs, aid the user in assessing whether the presented patient is in an altered state due to use of alcohol or drugs. As with other TACO SALAD links, any input by the user indicating that the patient may need more serious attention causes the system to prompt the user to reassess the situation or to lead the user to another treatment line. If the Alcohol and Drug links return negative responses, the user is directed to proceed to the green Standard Treatment line since no urgent clinical problems are indicated.

EXAMPLE 4

A user selects the green Standard line if the user determines that the presented situation is not life threatening or does not require urgent care. For example, if the child's eye injury appears to be a mild scratch and the child is calm. The user then properly selects the green Standard line to assess the presented situation. If the green Standard line is selected, the system presents the user with questions regarding the patient to aid the user in determining if any problems require redirection to the red Emergency, orange Very Urgent, or yellow Urgent lines. If no such indication is detected, the user is prompted to proceed along the green Standard line.

Figure 13:
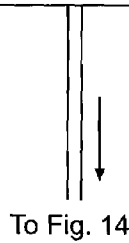
FIG. 13 is an example of a link for assessing a standard medical emergency.

Since the presented situation is determined not to be as urgent as in previous examples, the system allows the user more time to enter patient information. An example of a screen for entering this data is shown in FIG. 13. When entering patient information, the user is prompted to determine whether the presented patient has a high level of perception, or if the patient has a chronic underlying problem that caused the patient's arrival. If the patient is perceptive or if the patient's chronic problem has been exacerbated, the user is prompted to continue on the green Standard line. If the patient has a chronic problem that is not exacerbated, the system redirects the user to the low acuity blue line.

Figure 14:
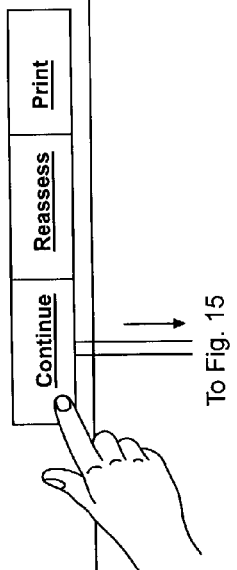
FIG. 14 illustrates a continuing link from FIG. 13 for further assessing a standard medical emergency.

When the user stays on the green Standard line, the system directs the user to the Green Zone Evaluation station, shown in FIG. 14. The Evaluation Station prompts the user to enter general patient information, such as date of birth, address, and marital status. Once the information is entered, the system prompts the user to proceed to the next station on the line. The next station, shown in FIG. 15, prompts the user to more thoroughly address the mental and physical characteristics of the patient. If the user inputs information that indicates an abnormal patient characteristic, such as agitation, the system directs the user to reassess the presented situation. If the characteristics entered by the user are normal, the user is prompted to print out assessment sheets showing the entered information.

Since the system forces the user to look at each symptom one at a time, the chance of underdiagnosing a patient is reduced. The user must properly pass through each station to progress to the next station on a selected line. Even though, the green Standard line is selected when the user is presented with less urgent conditions than the red, orange and yellow lines, the system requires the user to thoroughly travel the line. If the user does not complete the system requirements of the green line, the system prompts the user to reassess the presented situation, thereby assisting the user to become careful and cautious in diagnosis.

EXAMPLE 5

Since not every presented patient elicits an emergency response, the present invention also allows analysis of minor injuries, minor recurrent problems, or dormant problems. For instance, the example child with the eye injury may only have what appears to be pink eye. Also, if the presented patient appears normal and is not concerned with the eye, the user of the system selects the blue, Low Acuity line.

When the user is presented with a patient having a non-urgent, non-life threatening problem, the user selects the first station of the blue Low Acuity line, shown in FIG. 16. At the first station, the system prompts the user to enter more extensive personal information than required by the assessment features of previously mentioned, more urgent lines. However, it should be noted that the system preferably includes prompt questions such as: "Do you have any medical condition that may take your life right now?" to thereby assist the user in diagnosing any non-evident problems. In this way the system emphasizes user thoroughness.

After the user has entered initial patient information, the system directs the user to the next station, shown in FIG. 17. At this station, the user is directed to assess the presented patient's general state of being. The system prompts the user to answer questions regarding the presented patient's appearance. If the user enters a choice that indicates an abnormal condition, such as the patient having abnormal cognitive output, the system directs the user to reassess the situation. If no abnormal choices are entered, the user is directed to a station in which in-depth information regarding the presented patient is documented. As the user continues, the system prompts the user to answer additional questions regarding the presented patient. If at any time information is entered in the system that indicates that more urgent care is required, the system routes the user to the proper line. If no such information is entered, the system prompts the user to print the patient's assessment.

Although each of the assessment lines of the present system has been described separately, it should be noted that the each of the lines is integrated with the other lines. As FIG. 2 shows, the lines are intertwined. Since the present training system instructs a user to consider every step in diagnosing a presented patient, the user is taught proper assessment tools.

It should also be noted that the color scheme and groupings of information could be rearranged for different purposes. The present arrangement has been evaluated as being the most efficient system for teaching and reinforcing proper triaging skills.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

What is claimed:

1. A web-based training system for assisting a medical worker in timely diagnosis of a patient's symptoms, said system comprising:
    input means for entering data about a preselected patient;
    processing means for analyzing said data;
    a plurality of display screens, said display screens including hyperlinks, said hyperlinks facilitating analysis of said data, wherein at least one of said plurality of display screens comprises a mnemonic device for assisting said medical worker in diagnosing said patient's symptoms; and
    safeguards, said safeguards incorporated into said processing means, said safeguards assisting said medical worker to correctly diagnose said patient's symptoms.

2. The training system of claim 1 wherein said hyperlinks are linked to display screens, databases, and chat rooms.

3. The training system according to claim 1 wherein display screens are arranged according to severity of said patient's symptoms.

4. The training system according to claim 1 wherein the input means comprises a mouse.

5. The training system according to claim 1 wherein the input means comprises a touch screen.

6. The training system according to claim 1 wherein the input means comprises a keyboard.

7. The training system according to claim 1 wherein said safeguards hyperlink to at least one display screen of said plurality of display screens.

8. The training system according to claim 1 wherein said display screens are color-coded.

9. The training system according to claim 1 wherein said safeguards incorporated into said processing means further assist said medical worker from misdiagnosing said patient's symptoms.

10. A method for providing a user with training in medical triage, utilizing an interactive web based computer system having a video display, a user interface device, a website including a plurality of stored textual, audio and video display screens relating to decision making steps in medical triage, wherein a user selects from a plurality of available options relating to the various steps in triaging a hypothetical patient at a point of entry, said method comprising the steps of:
    (a) providing a web-based triage data base having a plurality of predetermined available options relating to said hypothetical patient on a first display screen, said available options arranged in related groupings, wherein at least one of said related groupings providing a mnemonic device for said user;
    (b) detecting which of the plurality of said predetermined available options was selected by the user with the user interface device;
    (c) displaying a second display screen of said plurality of display screens corresponding to the predetermined available action selected by the user; and
    (d) repeating steps (a) through (c) until either all scenarios relating to the hypothetical patient are exhausted or an erroneous available action is selected by the user.

11. The method of claim 10 wherein the plurality of predetermined available options provided in step (a) further include a plurality of erroneous triage actions for testing the user's knowledge of a triaging situation, and the method further comprising the steps of:
    providing a warning message on the first display screen upon the selection of an erroneous triage decision by the user; and
    providing a return option to enable the user to return to said previously displayed available options.

12. A web-based training system for assisting a medical worker in timely diagnosis of a patient's symptoms, said system comprising:
    input means for entering data about a preselected patient;
    a timer providing a predetermined amount of time for entering said data;
    an automated prompt to assist the medical worker in diagnosing the patient's symptoms, said automated prompt triggered when said predetermined amount of time of said timer expires;
    processing means for analyzing said data;
    a plurality of display screens, said display screens including hyperlinks, said hyperlinks facilitating analysis of said data, wherein at least one of said plurality of display screens comprises a mnemonic device for assisting said medical worker in diagnosing said patient's symptoms; and
    safeguards, said safeguards incorporated into said processing means, said safeguards assisting said medical worker to correctly diagnose said patient's symptoms.

13. The training system of claim 12 wherein said hyperlinks are linked to display screens, databases, and chat rooms.

14. The training system according to claim 12 wherein display screens are arranged according to severity of said patient's symptoms.

* * * * *